United States Patent [19] [11] 4,407,960
Tratnyek [45] Oct. 4, 1983

[54] VISUAL CHEMICAL INDICATING COMPOSITION FOR MONITORING STERILIZATION

[75] Inventor: Joseph P. Tratnyek, Sudbury, Mass.

[73] Assignee: American Sterilizer Company, Erie, Pa.

[21] Appl. No.: 162,811

[22] Filed: Jun. 25, 1980

[51] Int. Cl.$^3$ .................... G01N 21/06; C09K 3/34
[52] U.S. Cl. ..................... 436/1; 252/408.1;
116/206; 116/207; 422/55; 422/56; 422/57; 436/2; 436/93; 436/127; 374/162
[58] Field of Search ................ 252/408, 408.1; 116/206, 207; 73/356; 23/230 R, 230 D; 422/56, 57, 55; 436/1, 2, 93, 127; 374/161, 162

[56] References Cited

U.S. PATENT DOCUMENTS

| | | | |
|---|---|---|---|
| 3,258,312 | 6/1966 | Olson | 252/408 |
| 3,263,892 | 8/1966 | Danyi et al. | 116/206 |
| 3,627,469 | 12/1971 | Cheng | 252/408 |
| 3,852,034 | 12/1974 | Gunther | 252/408 |
| 3,974,180 | 8/1976 | Balli et al. | 116/207 |

FOREIGN PATENT DOCUMENTS

| | | | |
|---|---|---|---|
| 50-40475 | 4/1975 | Japan | 252/408 |
| 1405701 | 9/1975 | United Kingdom | 252/408 |

*Primary Examiner*—Teddy S. Gron
*Attorney, Agent, or Firm*—Robert D. Yeager

[57] ABSTRACT

An indicator system and device for visually monitoring ethylene oxide sterilization by color changes of the indicating composition of the system upon sufficient and properly conditioned exposure of the composition to ethylene oxide provides a controlled method for indicating the effective sterilization of articles by ethylene oxide. The indicating composition of this invention undergoes color changes that are progressive with the conditions and periods of sterilization, such that a final and complete color change indicates the completion of an effective ethylene oxide sterilization. The indicating composition comprises a leuco precursor of an aryl methane dye selected from the groups herein defined; and an acidic constituent. Acidic organic compounds such as diphenolic acid (4,4-bis [4-hydroxyphenyl] pentanoic acid) are effective acid constituents because they enhance hue, develop color and stabilize the final color change. The indicating composition is integrated into an indicator system and device further comprising a substrate or carrier and polymeric binder, any one or more of which may also provide wholly or in part the acidic constituent of the indicating composition. The indicator device in the form of a coated ticket or tape is disposed with the articles to be sterilized within an ethylene oxide sterilization chamber. Contact with ethylene oxide is maintained until a final color change, usually from a definite color to substantially colorless, occurs in the indicator, signifying the completion of an effective ethylene oxide sterilization of the articles.

11 Claims, No Drawings

VISUAL CHEMICAL INDICATING COMPOSITION FOR MONITORING STERILIZATION

BACKGROUND OF THE INVENTION

1. Field of the Invention

This invention relates to color changing compositions and devices that visually monitor a sterilization cycle.

2. Description of the Prior Art

Devices that contain chemical compositions that will change color when exposed to alkylating sterilants, such as ethylene oxide, under sterilization conditions are known as sterilization indicators. They are one means of monitoring the effectiveness of a sterilization process such as those cycles used in hospitals for sterilizing glassware, medical instruments and wrapped goods. Indicators are placed within the sterilization chamber inside or with the goods to be sterilized (load).

Color changes occur because of the reaction between the chemical ingredients in the indicator and the alkylating sterilant (i.e. ethylene oxide). The indicator is further designed so that the reaction will take place at the particular ethylene oxide concentration, moisture and temperature, that is required to achieve sterility in the load. It may also be adjusted to the time period of the particular sterilization cycle if this is desired.

It is therefore not adequate for an indicator just to change color when exposed to ethylene oxide; it must respond in an integrated manner to all of the parameters encountered in a sterilization cycle, specifically time, temperature, pressure, humidity and concentration of sterilant.

A popular means of monitoring ethylene oxide sterilization relies on detecting visually a pH change within an indicator; the pH changes are produced when ethylene oxide reacts with the specified chemical of the indicator in the presence of a pH sensitive dyestuff.

Other means of monitoring ethylene oxide sterilization depend on alkylation of a specified chemical by ethylene oxide to produce a color compound.

Some of the known chemicals utilized in indicators are substituted pyridines and isoquinolines, halide salts of metals, magnesium chloride, 4,4'(nitro-benzyl)pyridine, and triphenylmethanes.

Problems associated with prior indicators include:
(1) Weak or ambiguous color changes,
(2) Use of heavy metal salts or other toxic ingredients, and
(3) Measuring an induced change, such as pH rather than a direct sterilization effect of ethylene oxide.

Triphenylmethane dyes are part of a large, well-known group of commercially available organic synthetic dyes called the triarylmethane dyes. Triarylmethane dyes are derivatives of triphenylmethane $(C_6H_5)_3CH$ and diphenylnaphthylmethane $(C_6H_5)_2CH(C_{10}H_7)$ to which auxochromic and bathochromic (color producing) groups like amino ($NH_2$) and hydroxyl (OH) have been added. A triarylmethane dye is formed in substantially the following stages: formation of a colorless leuco base; conversion of the leuco base to the colorless carbinol or color base, and finally formation of the triarylmethane dye (which is a resonance hybrid radical-ion) by treatment (oxidation) with acid.

In the aldehyde method of preparation of triarylmethane dyes, an aromatic aldehyde provides the central carbon atom of the dye radical. Two moles of an aromatic amine are condensed with an aromatic aldehyde to yield the leuco base. The leuco base is oxidized to the carbinol base, which, in the presence of acid, is converted to the dye.

In a hydrol synthesis, the central carbon atom is supplied by a substituted benzhydrol, such as Michler's hydrol.

Thus a leuco base form and Michler's hydrol (which is termed an intermediate in a dye synthesis) are precursors in the formation of triarylmethane dyes. With the exception of the leuco base, crystal violet lactone, which has been used in the production of a new kind of carbonless copy paper, these precursors have not obtained end uses.

SUMMARY OF THE INVENTION

In the chemical indicating composition and device of this invention, it has been found that the dye-synthesis intermediate, Michler's hydrol, and the leuco bases can themselves be utilized, in the presence of acid, as visual indicating compositions for sterilization by an alkylating agent, such as sterilization by ethylene oxide.

The new indicating composition and system employing said composition of this invention monitors sterilization by ethylene oxide by chemical reactions of the composition with ethylene oxide that cause a visually perceptible color change from color to colorless. The color is unambiguous and irreversible. The composition is non-toxic to human beings, and the chemical reaction does not rely on an induced pH change.

The indicating composition of this invention comprises a selected precursor or analog thereof of a triarylmethane dye, and an acidic constituent. The precursor and acidic constituent react to produce a color (e.g. blue) which upon exposure to ethylene oxide under sterilization conditions will change to essentially colorless. Triarylmethane precursors effective for use as color change indicators herein are selected from the leuco base forms and dye-synthesis intermediates, and include: Michler's hydrol (4,4'-bis[dimethylamino]benzhydrol), Michler's hydrol leucobenzotriazole, Michler's hydrol leucomorpholine, Michler's hydrol leucobenzenesulfonamide, malachite green leuco, rhodamine lactam, crystal violet lactone, and crystal violet leuco.

The acidic conjugate compound functions to develop color, enhance hue, and stabilize the final color change. Acidic organic constituents such as the diphenolic acids are preferred, however, clay materials (or acid-earth materials) such as those found in paper substrates and acid-acting solvents, such as certain alcohols, will also provide an effective acidic environment.

The indicating composition is formed into an indicator system (or device) by the addition of a polymer which functions to regulate the permeability of the system to moisture and gas concentration, and thereby regulate the reaction rate. The polymer may also function as an adhesive for the composition. The system may be conveniently disposed on any inert receptive material or substrate such as cellulose blotter or silica gel.

The system, comprising triarylmethane precursor, acidic constituent, substrate (carrier) and polymer (polymeric binder) is disposed in the form of a coated ticket or tape in a sterilization chamber with the load to be sterilized. Sterilization by ethylene oxide is insured when a final color change to colorless occurs in the indicator.

DETAILED DESCRIPTION OF THE PREFERRED EMBODIMENTS

Structurally, the triarylmethane dye is an ionic compound with the chromophore, or color producing portion of the molecule, being a positive radical ion. This radical ion is actually a resonance hybrid, that is, it has a delocalized positive charge on the portion of the molecule. Resonance is considered the property of the molecule that is color producing. The triarylmethane dye may thus also be referred to as the dye radical or dye radical ion with reference to this color producing molecular structure.

The precursor leuco base-forms and the benzhydrol intermediates, (such as Michler's hydrol) from which the dye radical is derived, are non-resonating forms and therefore non-color producing. A leuco base precursor has a central saturated carbon atom, as does the intermediate, Michler's hydrol. The precursors herein used may be considered to be alkylated precursors of the triarylmethane dyes. The selected groups of leuco base and intermediates (also herein referred to as precursors) chosen for use in the indicating composition of the present invention include:

(i) Michler's hydrol,
(ii) Michler's hydrol leucomorpholine,
(iii) Michler's hydrol leucobenzotriazole,
(iv) Michler's hydrol leucobenzenesulfonamide,
(v) Malachite green leuco,
(vi) Rhodamine lactam,
(vii) Crystal violet leuco, and
(viii) Crystal violet lactone: all of which fall within the group identified structurally as:

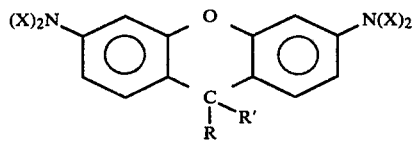

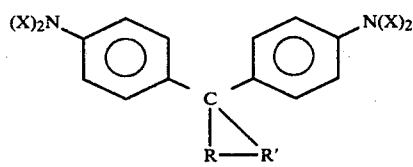

wherein x is selected from the group consisting of:

—CH$_3$, —C$_2$H$_5$;

and R is selected from the group consisting of:

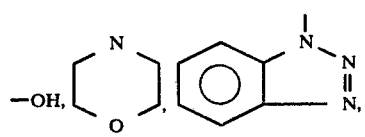

and R' is selected from the group consisting of:

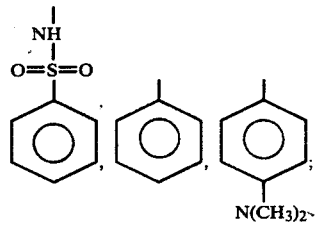

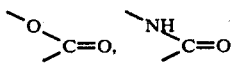

These colorless forms of the triarylmethane dye precursors require the presence of an acidic constituent to develop color. The exact chemical mechanism is unknown, but it is believed to involve attack at reactive sites in the leuco or intermediate molecule, resulting in a resonance hybrid with visible color. It is significant that the color producing resonance hybrid radical of this reaction cannot be used to resynthesize the original leuco or intermediate form in a reverse reaction. Thus the radical ion herein formed is not the radical ion of the known triarylmethane dyes. The color radical formed herein will undergo further reaction with an alkylating agent, such as ethylene oxide, to produce a final form which is again colorless. However again the final colorless composition or chemical cannot be hydrolized to the dye form reactant. The theoretical mechanism of the reaction of the chemical composition of the present invention is thus:

a known leuco base/intermediate is acidified to produce a colored unidentified dye-radical which in turn yields in the presence of ethylene oxide an unknown colorless form.

These leuco bases and intermediates are shown herein to be highly useful as ethylene oxide indicators, because the color formation is clear, unambiguous and stable; and a sharp colorless end point is reached when they react with ethylene oxide under sterilization conditions.

Because the leuco base forms and intermediates (precursors) are essentially available as crystalline solids, a solvent is required in their preparation for use as indicators. This solvent is used to dispose the precursors in solution on the substrate. It is critical that the solvent employed be essentially inert, or in any event not inhibitory of the color development. The solvent may contribute to the acidity environment or itself form the acid environment, as for example certain alcohols which may react as Lewis acids. It will also be appreciated that excess acidity can adversely affect color formation by reason of the reactive sites of the leuco bases and intermediates. This is especially the case for example with the use of Michler's hydrol, which has a highly reactive hydroxyl group and is therefore especially vulnerable to oxidative degradation. Acetone and methanol were the solvents of choice for applying the color active coating in the tests herein; choice of solvent is however variable within the above limitations.

Conditions applicable to choice of a solvent similarly apply to a choice of substrate or carrier material upon which the indicating composition is to be disposed. An inert carrier material may be utilized; or any acid-earth or clay material (such as found in paper), may be used which will cooperatively or independently function as the acidic constituent. Commercially available treated substrates such as polyester film having a surface of silica gel (pH 4–7.0) or cellulose blotters (pH 2–4.9) were predominately used as substrates herein.

As described above, the aforesaid substrates and solvents may function as the acidic constituent of the indicating composition of the present invention. However it was found that the use of the diphenolic acid, 4,4-bis(-4hydroxyphenyl)pentanoic acid, which is used in the preferred embodiment, is particularly effective as an acidic organic additive which develops color, stabilizes color and enhances hue.

The acid constituent of the present invention is in effect that which produces an environment for the reaction of the precursor chemical. This acid environment may be produced by (i) an acidic substrate such as acid-earth or clay with the addition of 4,4-bis(4hydroxyphenyl)pentanoic acid, such substrates having a pH range of 3.3 to 5.8; (ii) an originally neutral to slightly alkaline substrate (pH 7.0–7.5) that by acid-base ionization-reaction with a solvent becomes weakly acidic; (iii) an acidic substrate alone (the aforedescribed clays or acid-earths); or (iv) the solvent-substrate of (ii) with the addition of 4,4-bis(4hydroxyphenyl)pentanoic acid. In this acidic environment, produced by the reaction of substrate, solvent and/or acid, the colorless leuco precursors undergo bond-breaking resulting in the aforedescribed resonance which thereby produces color upon the surface of the substrate. When this is subsequently exposed to ethylene oxide under sterilization conditions as more specifically described below, the color changes to essentially colorless, indicating completion of a sterilization cycle. Because an indicating compound, composition system or device must be responsive to the total sterilization conditions of ethylene oxide, rather than the mere presence of ethylene oxide, all test data are derived from experiments carried out under suitable sterilization conditions which are defined in part by the following parameters:

| Time: | 1–3 hours |
| Temperature: | 67°–140° F. |
| Pressure: | 8–10 psig. |
| Relative humidity: | 30–100% |
| Ethylene oxide concentration in air: | 300–1200 mg/liter |

The term "exposure to ethylene oxide" is used herein to designate exposure to ethylene oxide under sterilization conditions.

The following specific sterilization conditions are standard for the experiments hereinafter described:

| Time: | 1.5 hours |
| Temperature: | 140° F. |
| Pressure: | 8–10 psig. |
| Chamber: | AMSCO Portagas Unit |

The precursor chemical was applied to the substrate from a solvent solution by saturating the substrate with about 5 drops of solution followed by air drying. The so-prepared test strips were then exposed to ethylene oxide, and observations of color and color changes were made. "Final" color as indicated in TABLE I designates color observed after several months of aging. Aging was utilized to determine the stability of color. Substrates are headed "Treated substrates" in reference to their specific function as indicator substrates which are commercially available, and the pH of the substrate is given in most instances because of its relevance to the acid reaction environment as discussed above.

In these specific examples, concentration of the precursor chemicals was in the range of 0.1–1.0 percent by weight of the solvent. Where 4,4-bis(4-hydroxyphenyl)-pentanoic acid was also added, the concentration of this acid was also in the range of 0.1–1.0 percent by weight of the solvent. Within this range, relative concentrations of the precursor and the acid did not materially affect the results.

The selected precursor compounds will produce color and color changes within broad parameters of an acidic environment that can be created either by the action or interaction of a solvent and a substrate, the substrate alone, or an acid additive. However, preferred reliability is achieved by their use as indicators within selected parameters of compounds and conditions shown to provide color and color changing results that are consistent, stable, and clearly defined. Therefore, the class of indicating compounds of this invention is further subdivided into sub-classes on the basis of respective conditions of preferred reliability. Details and examples are given below.

It will be apparent to those skilled in the art that quantitative as well as qualitative modifications of components within the composition and system will vary the color and color changing effects, as will the sterilization conditions under which they are practiced.

LEUCO CHEMICALS IN NON-ACID ENVIRONMENT

Referring now to Table I, leuco precursor chemicals, such as Michler's hydrol leucobenzenesulfonamide and Crystal Violet lactone (Test Nos. 1 and 2) do not undergo color change in a non-acid environment. In these examples, untreated filter paper was employed as a substrate and no 4,4-bis(4hydroxyphenyl)pentanoic acid was added. Therefore, the reaction environment was essentially neutral, and the criticality of acidity to color formation was demonstrated.

TABLE I

| CHEMICAL SOLVENT | TREATED SUBSTRATE | COLOR CHANGES WITH ETHYLENE OXIDE | | | COLOR CHANGES WITH ETHYLENE OXIDE AFTER ADDITION OF DIPHENOLIC ACID | | |
|---|---|---|---|---|---|---|---|
| | | BEFORE | AFTER | FINAL | BEFORE | AFTER | FINAL |
| 1. Michler's hydrol leucobenzenesulfonamide Acetone | Filter Paper | NONE | | | NO TESTS RUN | | |
| 2. Crystal Violet lactone Acetone | Filter Paper | NONE | | | NO TESTS RUN | | |
| 3. Michler's hydrol | Silica gel | lt. blue | yellowish | colorless | intense blue | lt. blue | gray- |

TABLE I-continued

| CHEMICAL SOLVENT | TREATED SUBSTRATE | COLOR CHANGES WITH ETHYLENE OXIDE | | | COLOR CHANGES WITH ETHYLENE OXIDE AFTER ADDITION OF DIPHENOLIC ACID | | |
|---|---|---|---|---|---|---|---|
| | | BEFORE | AFTER | FINAL | BEFORE | AFTER | FINAL |
| | Acetone (pH 7.4–7.5) | | | | | | |
| | Cellulose blotter (pH 4.2–4.9) | NONE | | | intense blue | lt. blue | colorless stable pale blue |
| | Polyamide (pH 4.6–5.0) | NONE | | | NO TESTS RUN | | |
| | Silica gel B (pH 4.8) | brt. blue | dull brown | yellowish | NO TESTS RUN | | |
| | Cellulose PEI (pH 2.9–3.2) | NONE | | | NO TESTS RUN | | |
| | Cellulose DEAE (pH 3.3–3.7) | green/blue | dull brown | yellowish | NO TESTS RUN | | |
| | Cellulose B (pH 4.8–5.4) | green/blue | dull brown | yellowish | NO TESTS RUN | | |
| | Aluminum Oxide (pH 5.2–5.7) | olive | dull brown | yellowish | NO TESTS RUN | | |
| 4. Michler's hydrol Ethanol | Silica gel (pH 7.4–7.5) | lt. blue | yellowish | colorless | intense blue | lt. blue gray | colorless |
| | Cellulose blotter (pH 4.2–4.9) | blue | yellowish | colorless | intense blue | lt. blue gray | stable pale blue |
| 5. Michler's hydrol Ethanol (in varying percents of Michler's hydrol) | Silica gel (7.4–7.5) | NONE | | | | | |
| | Cellulose blotter (4.2–4.9) | NONE | | | deep blue | lt. blue (Color only when % DPA is greater than % Michler's Hydrol) | |
| 6. Michler's hydrol leucomorpholine Acetone or Ethanol | Silica gel (7.4–7.5) | NONE | | | | | |
| | Cellulose blotter (4.2–4.9) | NONE | | | brt. blue | light blue | |
| 7. Michler's hydrol leucobenzenesulfonamide Acetone or Ethanol | Silica gel (7.4–7.5) | NONE | | | NONE | | |
| | Cellulose blotter (4.2–4.9) | NONE | | | brt. blue | light blue | almost colorless |
| 8. Michler's hydrol benzetriazole Acetone or Ethanol | Silica gel (7.4–7.5) | NONE | | | NONE | | |
| | Cellulose blotter (4.2–4.9) | NONE | | | brt. blue | pale blue | |
| 9. Crystal violet lactone Acetone or Ethanol | Silica gel (7.4–7.5) | brt. purple | pale violet | pale gray/purple | intense purple | almost colorless | |
| | Cellulose blotter (4.2–4.9) | NONE | | | deep blue | light blue | |
| 10. Crystal violet leuco Acetone or Ethanol | Silica gel (7.4–7.5) | brt. purple | pale blue | | intense violet | almost colorless | |
| | Cellulose blotter (4.2–4.9) | NONE | | | deep blue | pale blue | |
| 11. Rhodamine lactam Acetone | Silica gel (7.4–7.5) | light pink | colorless | | bright pink | very pale pink | |
| | Cellulose blotter (4.2–4.9) | NONE | | | | | |
| 12. Malachite green leuco Acetone or Ethanol | Silica gel (7.4–7.5) | blue | pale blue | colorless | NONE | | |
| | Cellulose blotter (4.2–4.9) | green/blue | pale blue | colorless | NONE | | |

MICHLER's HYDROL

Michler's Hydrol (4,4'-bis(dimethylamino)benzhydrol)

The composition consisting of the triphenylmethane dye intermediate, Michler's hydrol, and the acidic constituent, 4,4-bis(4hydroxyphenyl)pentanoic acid, is an excellent indicator for ethylene oxide sterilization, because as shown in Tests 3 and 4 of Table I, intense blue colors are formed which react with ethylene oxide to a precise, uniform, colorless and stable end point.

Also shown in Tests 3 and 4, Michler's hydrol on the paper (i.e. clay) substrates produce generally blue colors which change essentially colorless, (yellowish). While effective color change occured with the use of Michler's hydrol alone, the addition of 4,4-bis(4hydroxyphenyl)pentanoic acid produced more intense colors.

Acetone, methanol, were solvents used to apply the composition to the substrates. As seen in Test No. 5 of Table I, the solvent ethanol produced color only when the percent (by weight of solvent) of 4,4-bis(4hydroxyphenyl)pentanoic acid ("DPA" in the table) was greater than the percent (by weight of solvent) of Michler's hydrol.

In Test Nos. 3 and 4 of Table I, the concentrations of Michler's hydrol and 4,4-bis(4hydroxyphenyl)pentanoic acid were in the range of 0.1 to 0.5 percent by weight of the solvent. Within this range their relative concentration did not materially affect the color results. For percentage concentrations greater than 0.1 to 0.5 percent, the best relative concentrations of these components was determined to be in ratios in the range of 0.1–10 grams acid: 0.1–10 grams hydrol. At these proportions the color change is found to be from distinct colors of dark blue or blue-green to strongly contrasting pale blue or colorless. The most stable and intense blue colors are produced with high concentrations of 4,4-bis(4hydroxyphenyl)pentanoic acid relative to the Michler's hydrol. However, higher concentrations of Michler's hydrol (e.g. 10:1) also cause more saturated color.

MICHLER'S HYDROL LEUCOMORPHOLINE
Michler's Hydrol Leucobenzenesulfonamide
Michler's Hydrol Benzetriazole The compounds of this subclass of precursor chemicals have the following structural formulas:

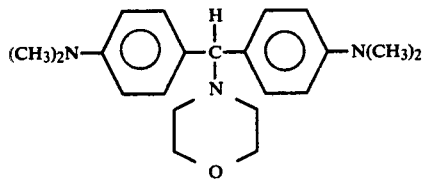

Michler's hydrol leucomorpholine

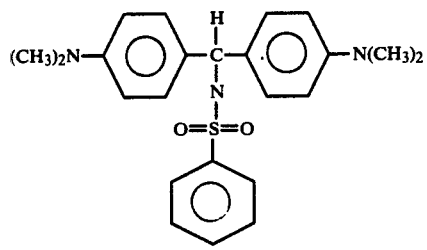

Michler's hydrol leucobenzenesulfonamide

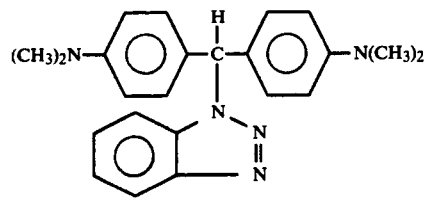

Michler's hydrol leucobenzotriazole

Michler's hydrol leucomorpholine, Michler's hydrol leucobenzenesulfonamide, and Michler's hydrol benzotriazole are leuco base precursors of the triarylmethane dyes which are derivatives of Michler's hydrol.

As shown on Table I, Test Nos. 5, 6, 7 and 8, these compounds also obtained preferred reliability with the addition of 4,4-bis(4hydroxyphenyl)acid. The operable relative concentration parameters of the leucochemical and 4,4-bis(4hydroxyphenyl)pentanoic acid were again in the range of 0.1 to 0.5 percent by weight of solvent; within this range relative concentrations of leucochemical to acid did not materially affect the color results. As shown in Table I, Test Nos. 6, 7 and 8; 4,4-bis(4hydroxyphenyl)pentanoic acid used with Michler's hydrol leucomorpholine, Michler's hydrol leucobenzenesulfonamide and Michler's hydrol benzetriazole in acetone or ethanol solvents produced bright blue colors which upon exposure to ethylene oxide faded to essentially colorless.

CRYSTAL VIOLET LACTONE
Crystal Violet Leuco

The leuco bases, crystal violet lactone and crystal violet leuco have the structural formulas:

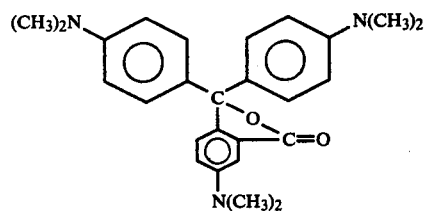

Crystal Violet lactone

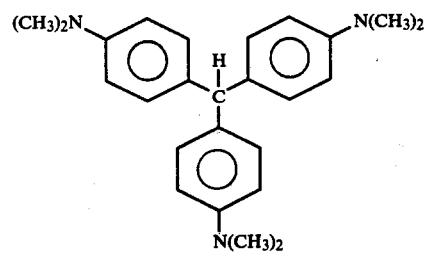

Crystal Violet leuco

As shown in Test Nos. 9 and 10 of Table I, these compounds produced strong purple hues in an acid environment which faded to pale colors on exposure to ethylene oxide. The addition of 4,4-bis(4hydroxyphenyl)pentanoic acid again intensified color effects achieved with substrate or substrate-solvent alone.

RHODAMINE LACTAM

The leuco chemical, rhodamine lactam has the structural formula:

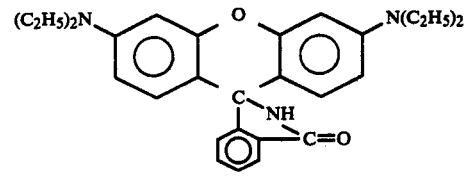

Rhodamine lactam produced pink hues which upon exposure to ethylene oxide faded to colorless. Again the addition of 4,4-bis(4hydroxyphenyl)pentanoic acid was effective in intensifying color and stabilizing color such that fading would not take place independently (without the ethylene oxide exposure). Preferred results where rhodamine lactam was used as an indicator were found to occur in an acid environment produced by an acid-earth substrate with acetone solvent, and the addition of 4,4-bis(4hydroxyphenyl)pentanoic acid. (Table I, Test No. 11).

MALACHITE GREEN LEUCO

Malachite green leuco has the structural formula:

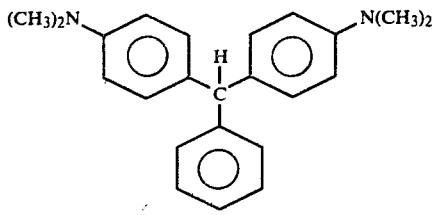

As shown in Table I, Test No. 12, malachite green leuco produced distinct blue to green-blue color in an acid environment achieved by substrate and/or substrate-solvent. The addition of 4,4-bis(4hydroxyphenyl)pentanoic acid under conditions of these tests was shown to inhibit color formation. The most constant and pronounced color change when using malachite green leuco as an indicator occured with the use of acetone or ethanol as the applicator solvent, and on an acid environment of clay substrate and/or substrate-solvent alone.

The aforedescribed triarylmethane dye precursors comprising the leuco base forms and Michler's hydrol intermediates have been shown to be effective for use as visual chemical indicators for ethylene oxide within the parameters and conditions set forth above. It is reasonable to conclude that analogs of the Michler's hydrol intermediates such as ethyl hydrol will react substantially the same as the methyl hydrol (Michler's). A unique end use has thus been presented for these precursors which in the presence of acid are applied as visual chemical indicating compositions for alkalylating agents such as ethylene oxide.

While the aforedescribed precursors were color producing, similar compounds tested were not effective even with the addition of 4,4-bis(4hydroxyphenyl)pentanoic acid. For example, triphenylmethane, triphenylamine, Michler's ketone, 2-nitrodiphenolamine, aurintricarboxylic acid and leucamine did not produce color or change color under any of the conditions herein utilized.

INDICATOR SYSTEM

The indicator system of this invention is achieved by integrating the indicating composition of this invention with a polymeric binder which, when applied to a substrate or carrier, forms a coated ticket or tape device.

The polymer coating obtains a desired response in the sterilization cycle. Properties of the chosen polymer, for example permeability to moisture and ethylene oxide are adjusted to regulate the rate of the reaction between the indicating composition and ethylene oxide.

The ticket or tape indicator system is disposed in a sterilizer chamber. The system functions in a chamber as an integrator for sterilization, in that when the colorless end point is reached in the indicating composition (thereby in the ticket or tape) the conditions for sterilization have been achieved in the chamber. The system (i.e. the reaction rate) may be adjusted to suitable predetermined sterilization conditions, such as time, humidity or concentration of ethylene oxide.

Preferred embodiments of the indicator system are those indicator compositions comprising Michler's hydrol and the acidic constituents shown in Table II. Compositions of the indicator system are set forth in grams of materials used. Systems 1 and 2, in Table II use alcohol soluble nylon as a polymeric binder with the solvent methanol, 4,4-bis(4hydroxyphenyl)pentanoic acid, and Michler's hydrol on substrates (clay containing paper) in the pH range of 4.1–6.3. In system 2, styrene-maleic anhydride resin is utilized as the organic acid constituent. This provides an indicator system that changes from a dark blue to colorless on sterilization by ethylene oxide. Systems 3 and 4 of Table II utilize ethyl cellulose as the polymeric binder. System 3 comprises ethyl cellulose, acetone as a solvent with 4,4-bis(4hydroxyphenyl)pentanoic acid and Michler's hydrol. System 4 comprises ethyl cellulose, methylene chloride and acetone as solvents 4,4-bis(4hydroxyphenyl)pentanoic acid, silica as an acidic binder modifier and Michler's hydrol.

It is noted that in the systems herein set forth the solvent, which although significant as discussed in the reactions above, is used in the initial application of the composition to the substrate and subsequently evaporates. Thus it is not an integral component of the indicator system. The use of silica as an acidic binder modifier is essentially another means by which acid-earth or clay is introduced into the system.

TABLE II

| | INDICATOR SYSTEMS | | | |
|---|---|---|---|---|
| | 1 | 2 | 3 | 4 |
| Alcohol soluble nylon | 2g | 2g | | |
| Ethyl Cellulose | | | 5g | 2g |
| Styrene-maleic anhydride resin | | 1.0g | | |
| Silica | | | 5.0g | 5.0g |
| 4,4-bis (4 hydroxyphenyl) pentanoic acid | 1.0g | | 1.0g | 1.0g |
| Michler's hydrol | 0.05g | 0.05g | 0.05g | 0.05g |
| Methanol | 48g | 48g | 9g | |
| Acetone | | | 36g | 10g |
| Methylene chloride | | | | 38g |
| Clay-containing Substrates | Coated boxboard: (pH 4.1–4.7) Coated paper cover stock: (pH 4.7–4.9) Shiny coated paper stock: (pH 5.7–6.3) | | | |

What is claimed is:

1. A chemical indicating composition for visually monitoring ethylene oxide sterilization comprising: the reaction product of (i) at least one indicator compound selected from the group consisting of Michler's hydrol, crystal violet lactone, malachite green leuco and crystal violet leuco and (ii) an acidic material selected from the group consisting of acid-earths and diphenolic acids; said reaction product being in the presence of ethylene oxide.

2. A chemical indicating composition as recited in claim 1 wherein: said reaction product is deposited upon a substrate.

3. A chemical indicating composition as recited in claim 2 wherein: said substrate has a pH range of 3.3 to 5.8.

4. A chemical indicating composition as recited in claim 1 wherein: said reaction product is contained in a polymeric binder that is permeable at a finite rate to ethylene oxide.

5. A chemical indicating composition as recited in claim 1 wherein: said indicator compound is Michler's hydrol.

6. A chemical indicating composition as recited in claim 1 wherein: said indicator compound is malachite green leuco.

7. A chemical indicating composition as recited in claim 6 wherein: said acidic material has a pH range of 3.3 to 5.8.

8. A chemical indicating composition as recited in claim 1 wherein:
said acidic material is 4,4-bis(4hydroxyphenol)pentanoic acid.

9. A chemical indicating composition as recited in claim 1 wherein:
said indicator compound is Michler's hydrol and said acidic material is 4,4-bis(4hydroxyphenol)pentanoic acid in concentration greater than that of the Michler's hydrol.

10. A chemical indicating composition for visually monitoring ethylene oxide sterilization comprising:
at least one indicator compound selected from the group consisting of Michler's hydrol, crystal violet lactone, malachite green leuco and crystal violet leuco; and 4,4-bis(4hydroxyphenol)pentanoic acid.

11. A method for visually monitoring ethylene oxide sterilization comprising the steps of:
introducting into a sterilization chamber the reaction product of
(i) at least one indicator compound selected from the group consisting of Michler's hydrol, crystal violet lactone, malachite green leuco and crystal violet leuco, and
(ii) an acidic material selected from the group consisting of acid-earths and diphenolic acids;
contacting said reaction product with ethylene oxide; and observing the presence or absence of an irreversible color change in said reaction product.

* * * * *

UNITED STATES PATENT AND TRADEMARK OFFICE
CERTIFICATE OF CORRECTION

PATENT NO. : 4,407,960
DATED : October 4, 1983
INVENTOR(S) : Joseph P. Tratnyek

It is certified that error appears in the above—identified patent and that said Letters Patent is hereby corrected as shown below:

Col. 1, line 56, delete "$(C_6H_5)_3CH$" and substitute therefor --$(C_6H_5)_3$ 3CH--; and Col. 7, after line 51, and before line 52, insert --, has the structural formula:

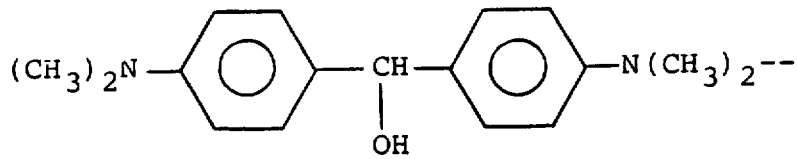

Col. 11, line 35, delete "ducing," and substitute therefor --ductive,--.

Signed and Sealed this

Fourth Day of December 1984

[SEAL]

Attest:

GERALD J. MOSSINGHOFF

Attesting Officer          *Commissioner of Patents and Trademarks*